Sept. 30, 1969 P. ECKE Plant Pat. 2,924
POINSETTIA PLANT
Filed Feb. 27, 1968
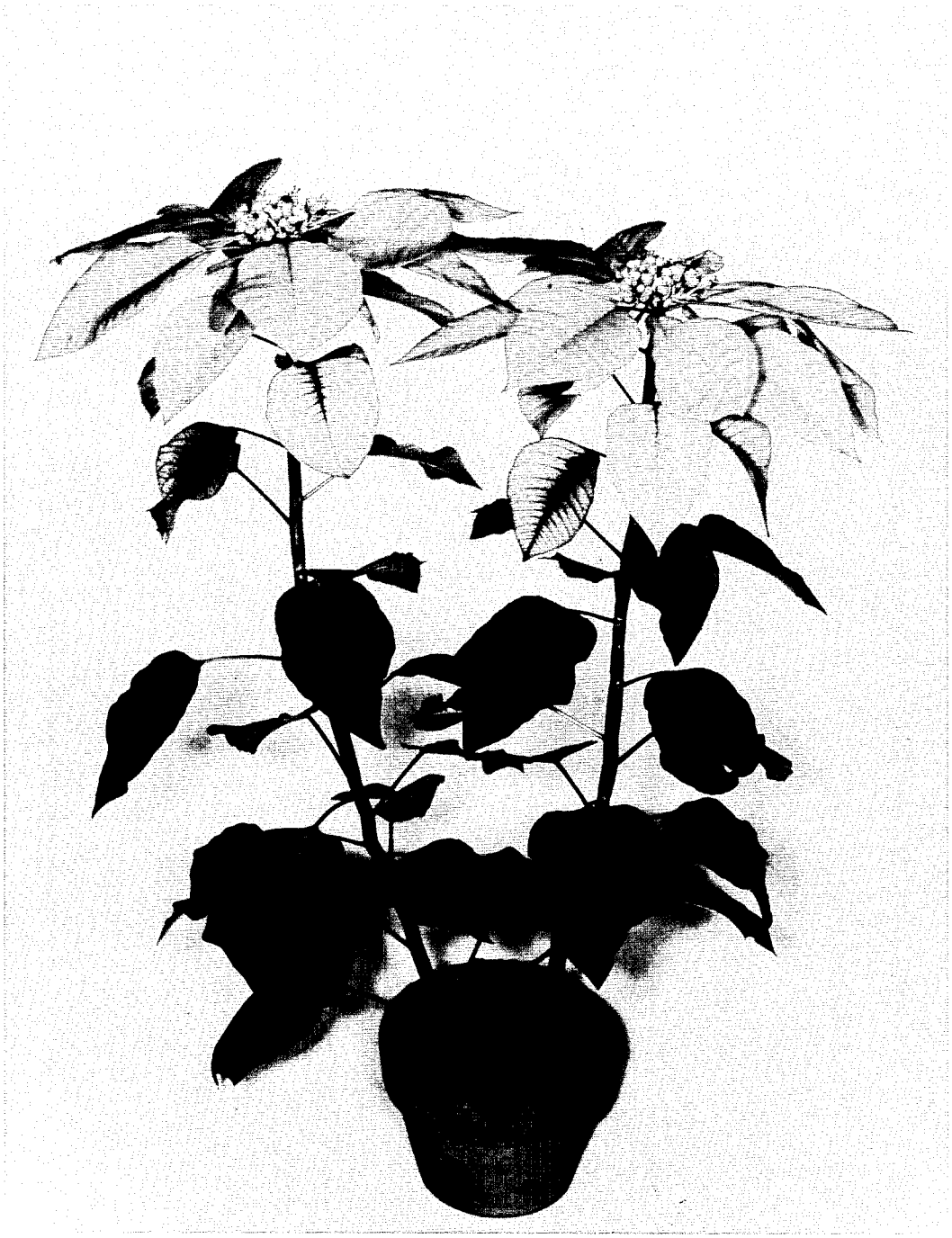
Inventor.
Paul Ecke
By: Robb & Robb
Attorneys.

United States Patent Office

Plant Pat. 2,924
Patented Sept. 30, 1969

2,924
POINSETTIA PLANT

Paul Ecke, Encinitas, Calif., assignor to Paul Ecke, Inc., Encinitas, Calif., a corporation of California Filed Feb. 27, 1968, Ser. No. 708,729
Int. Cl. A01h 5/12
U.S. Cl. Plt.—86 1 Claim The present invention relates to a new and distinct variety of poinsettia plant (botanically known as *Euphorbia pulcherrima*), which was originated by me by crossing an unnamed and unpatented pink poinsettia seedling with the variety known as "Mikkelpink" (Plant Patent No. 2,501), the former being the seed parent and the latter being the pollen parent.

The primary objective of this breeding were to produce an early blooming variety which matures into full bloom earlier than other known commercial varieties, and to produce a new variety which has stiff stems and does not require staking, which has great depth in appearance, and a greater number and a distinctive arrangement of bracts, some of which extend down the stem, giving a more full appearance. These objectives were fully achieved, along with other desirable features, as evidenced by the following unique combination of characteristics which are outstanding in the new variety and which distinguish it from its parents, as well as from all other varieties of which I am aware:

(1) A very vigorous, tough and durable plant habit;
(2) Stiff stems which do not require staking;
(3) A very vigorous and extensive root system;
(4) Attractive, vivid bright red bracts, extending down the stem, with some bracts extending in an upward plane giving a slightly cupped appearance, with the total presentation giving a greater depth in appearance;
(5) A short growing habit when grown naturally;
(6) An exceptionally well-pinching habit which produces an unusually large number of breaks, usually more than 4;
(7) A compact, bright and exaggerated flower center giving a crowned effect to each bloom, said center of the flower corresponding in color to Chrome Yellow;
(8) An early blooming habit, usually 8 weeks after start of short days, but having the ability to be satisfactorily brought into bloom and full maturity in every month of the year through exercise of proper greenhouse cultural techniques;
(9) A distinctive and attractive general color tonality of the bracts corresponding to Currant Red;
(10) Absence of drooping and retention of the inflorescence position relative to the bracts without rising as occurs in other varieties as the inflorescence approaches maturity;
(11) Exceptional suitablity for the production of multiple bloom plants; and
(12) Excellent keeping qualities and consequent suitability for home decoration.

A sexual reproduction of my new variety by vegetative cuttings propagated under mist at Encinitas, Calif., shows that the foregoing characteristics and distinctions come true to form and are established and transmitted through succeeding propagations.

The accompanying drawing shows a typical specimen plant of my new variety as depicted in color as nearly true as it is reasonably possible to make the same in a color illustration of this character.

The following is a detailed description of my new poinsettia variety, with color terminology in accordance with Wilson's Horticultural Colour Chart, except where general color terms of ordinary dictionary significance are obvious, as based on specimens grown at Encinitas, Calif., under regular commercial practices:

Parentage: Seedling.
*Seed parent.*—An unnamed and unpatented pink seedling.
*Pollen parent.*—"Mikkelpink."

Propagation: Holds its distinguishing characteristics through succeeding propagations by vegetative cuttings.

Form: Medium height; upright; graceful contour.

Habit of growth: Vigorous grower but not too tall.

Rooting habit: Medium fast (from 15 to 20 days under mist); extensive; uniform.

Blooming habit: Blooms at an earlier date than other commercial varieties.

Blooming season: Matures to full bloom rapidly (approximately 8 weeks after start of short days) but has excellent suitability for forcing in every month of the year by appropriate greenhouse culture practices.

Foilage: Alternate; borne horizontally on stems; persistant; normal quantity.
*Size.*—Small (from about 2½ inches to 5 inches long); width from about 2½ inches to 4 inches.
*Shape.*—Both serrated and nearly oval.
*Texture.*—Upper side—Semi-glossy; ordinary recessed veins. Under side—dull; ordinary protruding veins.
*Margin.*—Well defined.
*Color.*—New foilage: upper side—near Sage Green, Plate 000861/1, page 198; lower side—near Sage Green, Plate 000861/2, page 198. Old foilage: upper side—near Ivy Green, Plate 0001060/2, page 200; lower side—near Sage Green, Plate 000861/2, page 198.

Disease resistance: Resistant to rhizoctonia and pythium stem and root rot during propagation and growing period, and resistant to botrytis during blooming period, as determined by comparison with other plants grown under the same cultural conditions at Encinitas, Calif., which are infected with these diseases.

Bracts: Many (approximately 18–20 in number); medium length; medium width; good retention; many layered; new bracts form and develop as other bracts mature; normal lasting qualities; short pointed when young, becoming somewhat wider at maturity; retain relative position and do not droop, with some of the upper bracts extending in an upward plane giving a slightly cupped appearance when mature or as bracts continue to age giving a symmetrical appearance to the bracts; retain their color exceptionally well; nearly smooth in appearance; have very short petioles giving a very full appearance. Color: upper side—near Currant Red, Plate 821/3, page 167; lower side—near Rose Opal, Plate 022/1, page 110.

Flowers:
*Borne.*—Many flowers per stem in regular clusters in varying stages of development; borne on strong, very short stems; normal development; total inflorescence gives a tight and compact appearance giving an exaggerated form which creates an attractive crowned effect in each bloom.
*Quantity of bloom.*—Relatively abundant; flowers gradually drop off after maturity but new ones continue to develop as flower stems continue to grow.
*Buds.*—From small to medium size; born on light green stems. Color—near Lettuce Green, Plate 861/3, page 176.

Reproductive organs:
*Stamens.*—Few; from about ⅛ inch to ¼ inch long. Color—near Claret Rose, Plate 021, page 109.
*Pollen.*—Color—near Naples Yellow, Plate 403, page 121.
*Styles.*—Color—near Rose Opal, Plate 022, page 110.

*Ovaries.*—Color—near Lettuce Green, Plate 861/2, page 176.

*Nectar cups.*—Unusually bright color. Color—Chrome Yellow, Plate 605, page 144.

General observations: As compared with the unnamed seed parent, the new variety principally differs from this parent in that the new variety is lower growing and the color of the new variety is red whereas the seed parent variety is taller and the color is pink. As compared to its pollen parent "Mikkelpink," the new variety principally differs from this parent in that its color is red whereas the pollen parent variety color is pink.

I claim:

1. A new and distinct variety of poinsettia plant, substantially as herein shown and described, characterized particularly as to novelty by the unique combination of a very vigorous, tough and durable plant habit, stiff stems which do not require staking, a very vigorous and extensive root system, attractive, vivid bright red bracts extending down the stem, with some bracts extending in an upward plane giving a slightly cupped appearance, with the total presentation giving a greater depth in appearance, a short growing habit when grown naturally, an exceptionally well pinching habit which produces an unusually large number of breaks, usually more than 4, a compact, bright and exaggerated flower center giving a crowned effect to each bloom, said center of the flower corresponding in color to Chrome Yellow, an early blooming habit, usually 8 weeks after start of short days, but having the ability to be satisfactorily brought into bloom and full maturity in every month of the year through exercise of proper greenhouse cultural techniques, a distinctive and attractive general color tonality of the bracts corresponding to Currant Red, absence of drooping and retention of the inflorescence position relative to the bracts without rising as occurs in other varieties as the inflorescence approaches maturity, exceptional suitability for the production of multiple bloom plants, and excellent keeping qualities and consequent suitability for home decoration.

No references cited.

ROBERT E. BAGWILL, Primary Examiner